(12) United States Patent
Auguste et al.

(10) Patent No.: US 9,597,234 B2
(45) Date of Patent: *Mar. 21, 2017

(54) VERY ABSORBENT, THIN ADHESIVE DRESSING, AND USES THEREOF FOR THE TREATMENT OF CHRONIC WOUNDS

(75) Inventors: Stéphane Auguste, Ruffey les Echirey (FR); Jean-Marc Pernot, Dijon (FR); Anne-Sophie Danerol, Dijon (FR); Aurelie Charre, Montanay (FR)

(73) Assignee: URGO RECHERCHE INNOVATION ET DEVELOPMENT, Chenove (FR)

( * ) Notice: Subject to any disclaimer, the term of this patent is extended or adjusted under 35 U.S.C. 154(b) by 661 days.

This patent is subject to a terminal disclaimer.

(21) Appl. No.: 14/111,851

(22) PCT Filed: Apr. 13, 2012

(86) PCT No.: PCT/FR2012/050812
§ 371 (c)(1),
(2), (4) Date: Jan. 8, 2014

(87) PCT Pub. No.: WO2012/140378
PCT Pub. Date: Oct. 18, 2012

(65) Prior Publication Data
US 2014/0114268 A1    Apr. 24, 2014

(30) Foreign Application Priority Data
Apr. 15, 2011  (FR) .................... 11 53327

(51) Int. Cl.
*A61M 27/00*   (2006.01)
*A61F 13/15*   (2006.01)
(Continued)

(52) U.S. Cl.
CPC .......... *A61F 13/0206* (2013.01); *A61F 13/02* (2013.01); *A61F 13/022* (2013.01);
(Continued)

(58) Field of Classification Search
CPC ............ A61F 13/00; A61F 2013/00089; A61F 2013/00238; A61F 2013/00255;
(Continued)

(56) References Cited

U.S. PATENT DOCUMENTS 4,921,704 A    5/1990  Fabo
6,023,008 A    2/2000  Mahoney et al.
(Continued)

FOREIGN PATENT DOCUMENTS

EP    0299122    7/1987
EP    0251810    1/1988
(Continued)

*Primary Examiner* — Jacqueline Stephens
(74) *Attorney, Agent, or Firm* — Hamre, Schumann, Mueller and Larson, P.C.

(57) ABSTRACT

The invention relates to an absorbent dressing comprising an adhesive silicone-coated side strip, which is particularly suitable for use in the care of chronic wounds, such as ulcers or eschars, or acute wounds, such as burns.

The absorbent dressing includes a breathable impermeable substrate (4) and an absorbent non-woven fabric (6). The substrate is formed by assembling a continuous film (4*a*) and an openwork reinforcement that is coated with an adhesive silicone gel (4*b*) without blocking the openings in the reinforcement. A non-absorbent web (5) is secured to a complementary non-woven fabric (7), such as to encase the above-mentioned absorbent non-woven fabric (6) without being secured at any point to the latter. The encased absorbent non-woven fabric is subsequently assembled to the substrate (4) along part of said silicone-coated surface of the substrate.

12 Claims, 1 Drawing Sheet

(51) Int. Cl.
*A61F 13/00* (2006.01)
*A61F 13/02* (2006.01)

(52) U.S. Cl.
CPC ........ *A61F 13/023* (2013.01); *A61F 13/0209* (2013.01); *A61F 13/0213* (2013.01); *A61F 13/0223* (2013.01); *A61F 13/0226* (2013.01); *A61F 13/0279* (2013.01); *A61F 13/0283* (2013.01); *A61F 13/0289* (2013.01); *A61F 2013/0077* (2013.01); *A61F 2013/00089* (2013.01); *A61F 2013/00225* (2013.01); *A61F 2013/00229* (2013.01); *A61F 2013/00238* (2013.01); *A61F 2013/00255* (2013.01); *A61F 2013/00259* (2013.01); *A61F 2013/00604* (2013.01); *A61F 2013/00702* (2013.01); *A61F 2013/00719* (2013.01); *A61F 2013/00723* (2013.01); *A61F 2013/00774* (2013.01); *A61F 2013/00778* (2013.01); *A61F 2013/00782* (2013.01)

(58) Field of Classification Search
CPC .. A61F 2013/00259; A61F 2013/00774; A61F 2013/00778; A61F 2013/00782
USPC .................................. 604/543, 365; 602/44
See application file for complete search history.

(56) References Cited

U.S. PATENT DOCUMENTS

| | | | |
|---|---|---|---|
| 6,096,942 | A | 8/2000 | Hack |
| 6,881,875 | B2 | 4/2005 | Swenson |
| 2004/0241214 | A1 | 12/2004 | Kirkwood et al. |
| 2009/0216168 | A1 | 8/2009 | Eckstein |
| 2010/0292626 | A1 | 11/2010 | Gundersen et al. |
| 2012/0095380 | A1 | 4/2012 | Gergely et al. |

FOREIGN PATENT DOCUMENTS

| | | |
|---|---|---|
| EP | 0300620 | 1/1989 |
| EP | 0358412 | 3/1990 |
| EP | 0392788 | 4/1990 |
| EP | 0420515 | 9/1990 |
| WO | 9304101 | 3/1993 |
| WO | 9429361 | 12/1994 |
| WO | WO 96/01659 | 1/1996 |
| WO | 9616099 | 5/1996 |
| WO | WO 2004/064879 | 8/2004 |
| WO | 2004074343 | 9/2004 |
| WO | WO 2008/012443 | 1/2008 |
| WO | WO 2008/146529 | 12/2008 |
| WO | 2009130485 | 10/2009 |
| WO | WO 2010/147533 | 12/2010 |

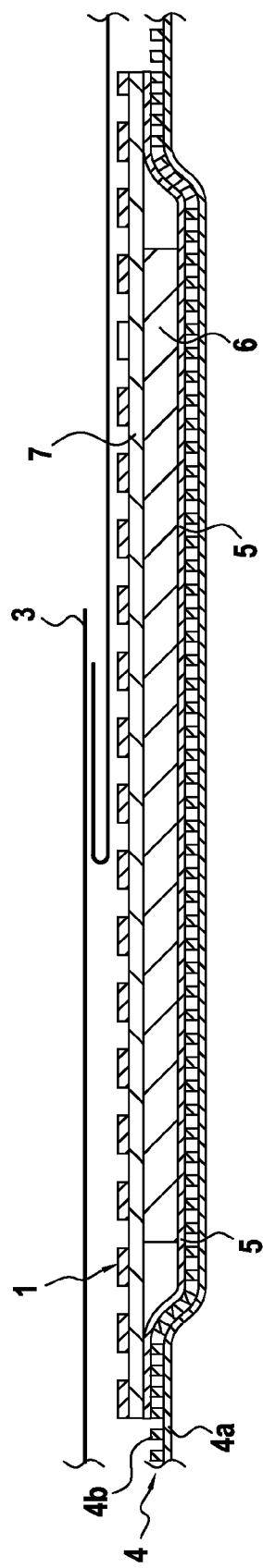

VERY ABSORBENT, THIN ADHESIVE DRESSING, AND USES THEREOF FOR THE TREATMENT OF CHRONIC WOUNDS

The present invention relates to an adhesive dressing comprising a breathable impermeable protective substrate and an absorbent nonwoven, and also to the use thereof in the care of chronic or acute wounds, for which the perilesional skin is particularly weakened.

Adhesive absorbent dressings comprise at least one adhesive border, which can take the form of a "side strip", and allows the dressings to be secured to the skin which surrounds the wound. These dressings, in particular when they are used for the treatment of particularly painful chronic wounds, are advantageously conformable and thin in order to limit the tensions that the dressing can create at the surface of the skin. They must also be very absorbent. In the care of wounds of this type, it is preferable to use dressings in which the side strip is covered with a silicone adhesive, which is more friendly to the weak and sensitive perilesional skin.

Absorbent dressings exist which comprise the assembly of an absorbent foam and a breathable impermeable protective substrate. The protective substrate is impermeable to fluids and to external pathogenic microorganisms, but permeable to water vapor, so as to avoid contact of the wound with liquids and bacteria and maceration of the wound. The thickness of the absorbent foams is chosen according to the desired exudate absorption capacity and retention capacity, so that it will be necessary to choose a very thick foam in order to obtain a very absorbent dressing.

In the Mepilex® Border product, it has therefore been proposed to assemble an absorbent nonwoven to the foam in order to reduce the total thickness of the dressing without reducing its absorption capacity. The manufacture of this structure comprising two different absorbent materials is, however, more complex to carry out, and the silicone adhesive covers the entire surface of the dressing.

However, in this dressing structure, the silicone gel is in direct contact with the wound, and the fact that the silicone adhesive covers the entire surface of the dressing does not make it possible to specifically adapt the interface layer which may cover the surface of the absorbent foam. Finally, in such a dressing, the adhesive-coated substrate does not act as a side strip.

This discontinuous structure of the silicone gel makes it possible to avoid having to secure the silicone gel, once crosslinked, to the absorbent layer of the dressing. Indeed, the silicone gel once crosslinked cannot be secured in a long-lasting manner to an absorbent foam commonly used in the manufacture of a dressing comprising an adhesive side strip.

There is therefore a need to produce a very absorbent dressing in which only the surface of the side strip is covered with a silicone adhesive, and the structure of which comprises an absorbent compress so as to dispense with the use of a foam, in order to obtain a dressing which is even thinner.

Some absorbent compresses have the drawback of breaking up and of increasing greatly in volume as exudates are absorbed, so that it is necessary to encase them. The encasement of the compress, which is generally a nonwoven, must meet certain criteria, including access of the exudates to the compress and long-lasting securing of the casing to the breathable impermeable substrate used. Thus, the size of the casing must allow expansion of the nonwoven during the absorption of the wound exudates, and the casing must not detach from the substrate when it becomes moist in contact with the exudate-loaded compress. The risks of leakage of liquids and of delamination of the various layers constituting the dressing must be avoided.

In patent application EP 358 412, for example, the dressing comprises, a superabsorbent air-laid of cellulose pulp comprising polyethylene fibers and superabsorbent particles. This compress is encased in a nonwoven before being adhesively bonded, using an acrylic adhesive, to the center of a substrate, which can consist of two materials, a polyethylene plastic film adhesively bonded, using an acrylic adhesive, to a polyester or polypropylene nonwoven. However, this dressing is not more suitable for use in the care of chronic or acute wounds, essentially for two reasons: the polyethylene substrate is not breathable and the acrylic adhesive applied to the border can damage particularly weakened perilesional skin.

In document U.S. Pat. No. 6,096,942, the absorbent compress is encased in a polyester fiber nonwoven. The borders of the polyester nonwoven are sealed in such a way that the compress remains confined in a closed compartment, without being attached to the casing. The substrate layer of the dressing is a flexible polyurethane film, that is permeable to water vapor, but impermeable to liquids, and that is coated over its entire surface with an acrylic adhesive in order to adhesively bond to the polyester casing. This dressing comprises an acrylic adhesive side strip; however, as has been explained above, it is preferable to avoid contact of an acrylic adhesive with the skin in the treatment of chronic wounds.

The production of very absorbent adhesive dressings must meet complex specifications and reconcile contradictory characteristics. The main criteria that such a dressing must establish are essentially those of having good breathability while at the same time avoiding the risks of leaking and of maceration, of being impermeable to liquids and to bacteria, of being breathable (i.e. permeable to water vapor), of remaining cohesive when it is removed once loaded with exudates, of being thin in order to limit the discomfort that can be caused by the dressing applied to the skin, and of being easy to manufacture.

The dressing must also be easy to apply and remain in place for as long as possible without being detrimental to the perilesional skin, have a high absorption capacity, and not impair the healing of the wound when it is removed. The dressing must also mold to the morphology of the patient and be compatible with the complementary use of a support system. It must also be as flexible as possible, and not become stiff during the absorption of wound exudates.

The choice of the materials which constitute the dressing, the arrangement of the materials with respect to one another, and the means for assembling the latter are very complex if all these properties are to be obtained at the same time.

The object of the present invention is to provide novel adhesive absorbent dressings comprising an absorbent nonwoven and a substrate that is impermeable, but highly permeable to water vapor, which are easier to manufacture than the prior art dressings of this type, which are very thin, which remain cohesive under dry conditions but also moist conditions, and the adhesive side strip of which is coated with an adhesive silicone gel.

The invention provides in particular a novel means for securing an absorbent nonwoven to a substrate comprising an openwork reinforcement that is coated with adhesive silicone gel without blocking the openings of the reinforcement, without reducing the breathability properties of the substrate, without reducing the absorption capacities of the absorbent nonwoven, and without reducing the cohesion of the dressing.

A subject of the invention is thus an adhesive absorbent dressing comprising an absorbent nonwoven and a protective substrate that is impermeable to fluids, but permeable to water vapor, such that:

the substrate is formed by assembling a continuous film and an openwork reinforcement that is coated, on at least one of its faces, with adhesive silicone gel without blocking the openings in the reinforcement, said reinforcement covering the entire surface of the film, said dressing also comprises a non-absorbent web and a complementary nonwoven which are secured to one another along their periphery while encasing said absorbent nonwoven, preferably without being secured at any point to the latter, and the non-absorbent web adheres to the adhesive silicone gel that is coated onto said reinforcement.

The non-absorbent web is an essential element of the invention since a substrate that is coated with a silicone gel over its entire surface, and in particular discontinuously, cannot be directly secured to the encased absorbent nonwoven. The encased absorbent nonwoven also cannot be assembled to the substrate using an acrylate adhesive when it is coated with silicone gel.

Such dressings are, for example, represented in cross section in the appended FIGURE.

The FIGURE represents an embodiment of the invention, in which the absorbent nonwoven 6 comprises cellulose-based fibers and particles of superabsorbent polymer.

The absorbent nonwoven 6 is successively covered on the side facing the wound:

with a complementary nonwoven 7, which does not disintegrate when it comes into contact with the exudates, and which prevents the fibers and the particles of superabsorbent polymer contained in the absorbent nonwoven 6 from contaminating the wound, with a discontinuous interface layer 1 consisting of an elastomer-based composition containing particles of hydrocolloid, which is itself protected by a peel-off protector 3.

The complementary nonwoven is placed on the side closest to the wound. The substrate layer 4 is formed by assembling a film 4a that is impermeable to liquids, but permeable to water vapor, and an openwork reinforcement that is coated with an adhesive silicone gel 4b without blocking the openings in the reinforcement. The substrate layer 4 is secured to the absorbent nonwoven textile 6 by insertion of a non-absorbent web 5.

In this embodiment, the non-absorbent web 5 and the complementary nonwoven 7 are of equal size and are sealed along their edges, so as to encase the absorbent nonwoven 6, the size of which is smaller than that of the complementary nonwoven and of the non-absorbent web.

The substrate is preferably impermeable to fluids and to external pathogenic microorganisms, while at the same time providing permeability to water vapor, so as to avoid both contact of the wound with external liquids and bacteria and maceration of the wound. This is then referred to as a "breathable impermeable substrate".

The substrate is preferably thin and flexible, so as to mold better to the shape of the body and to follow the movements without risk of detaching. The substrate is advantageously conformable. Its thickness can be between 100 and 600 µm, and preferably between 250 and 500 µm.

The substrate which is part of the dressing according to the invention consists of a continuous film 4a and an openwork reinforcement that is coated with an adhesive silicone gel 4b without blocking the openings of the reinforcement. The film is continuous in the sense that it has not undergone a perforation step.

The film can be replaced with a foam/film complex or a textile/film complex. Among the usable films, mention may be made, by way of example, of polyether urethane, polyetheramide or polyether ester films.

The thickness of the film is, for example, between 5 and 200 microns, preferably between 10 and 75 microns and more preferably between 10 and 50 microns.

The continuous film is impermeable to liquids, but permeable to water vapor. The continuous film may be a breathable impermeable film or complex previously mentioned, such as those commonly used for manufacturing absorbent dressings. The film advantageously has a moisture vapor transmission rate (MVTR) greater than 3000 $g/m^2/24$ hours, preferably greater than or equal to 7000 $g/m^2/24$ hours and more preferably greater than or equal to 10 000 $g/m^2/24$ hours. The openwork reinforcement is coated with a silicone compound without blocking the openings of the reinforcement. This reinforcement thus coated is advantageously chosen in such a way that the value of the moisture vapor transmission rate of the substrate remains satisfactory, in particular greater than or equal to 4000 $g/m^2/24$ hours, preferably greater than or equal to 5000 $g/m^2/24$ hours. A technique for measuring the moisture vapor transmission rate in liquid contact is described in standard NF-EN 13726-2 (Chapter 3.3).

The reinforcement makes it possible to stiffen the substrate, in such a way that it does not roll up on itself after removal of a peel-off protector optionally used to protect the complementary nonwoven, the interface layer and/or the adhesive border.

The reinforcement may consist of any openwork material, such as a perforated film, a thermoplastic net, a textile, for instance a woven, a knit or a nonwoven, which is preferably elastic for a better hold of the dressing on the skin. A perforated film will, for example, be made of polyethylene or of polypropylene. A woven textile will, for example, be made of polyethylene terephthalate or of polyamide. The grammage of the reinforcement is preferably between 10 and 500 $g/m^2$, for example between 20 and 300 $g/m^2$. The reinforcement can be coated with silicone gel on one of its faces, on both its faces, or even on its entire surface. The size of the openings of the reinforcement can be between 0.1 and 5 mm, for example between 0.5 and 3 mm. The open surface of the reinforcement preferably represents from 1% to 99%, preferably from 25% to 90% and more preferably from 30% to 80% of the surface of the continuous film, and the open surface of the reinforcement once covered with silicone gel preferably represents from 10% to 99%, preferably from 10% to 60% and more preferably from 25% to 75% of the surface of the continuous film.

According to one embodiment, a knit, preferably a knit that is coated with silicone gel on its entire surface without blocking the openings of the knit, which may be advantageously adhesively bonded to the continuous film 4a, will be used.

According to another embodiment, the reinforcement is a perforated film that is coated with silicone gel on just one of its faces without blocking the perforations of the film, for example a perforated polyurethane film, which may be secured to the continuous film by heat, ultrasound, high frequency or an adhesive.

The adhesive silicone gel is a silicon compound of which the structure is crosslinked. The silicone gel exhibits a cohesion such that it does not leave residues on the skin and remains attached to the reinforcement when the dressing is removed. It can be manufactured from silicone precursors which crosslink after they have been brought into contact, following a hydrosilylation or condensation reaction. Such systems are known from the prior art, for example in documents EP-A-0 251 810, EP-A-0 300 620 or U.S. Pat. No. 4,921,704. The mixtures of precursors described in these documents comprise essentially:

a component A which comprises at least one polydimethylsiloxane substituted with a vinyl group at each of its ends, and a platinum catalyst, and a component B of polydimethylsiloxane which comprises at least two hydrosilane groups.

Bringing together the two components causes a crosslinking reaction of the two functionalized polydimethylsiloxanes which advantageously takes place at ambient temperature and can be accelerated by heat.

Additives such as pigments, inhibitors or bulking fillers can be incorporated into at least one of the two components.

The precursors of the adhesive silicone gel can be chosen from the following products: Silbione RT Gel® 4712 A&B and Silbione RT Gel® 4717 A&B from Bluestar Silicones, Wacker Silgel® 612 from Wacker-Chemie GmbH, Nusil® MED-6340, Nusil® MED-6345, Nusil® MED3-6300 or Nusil® MED12-6300 from Nusil Technology, and D-7-9800® from Dow Corning.

The silicone gel is preferably chosen in such a way that the substrate has an adhesive power on skin, according to the EN 1939 method, of greater than 40 cN/cm, and preferably 45 cN/cm. A substrate sample 20 mm wide and 150 mm long is placed on the forearm. After 10 minutes, the adhesive power is measured with a dynamometer at a tensile speed of 900 mm/min with an angle of 90°.

The silicone gel is preferably applied to the openwork reinforcement without blocking the openings of the reinforcement at a grammage of between 100 and 500 g/m$^2$, preferably between 150 and 250 g/m$^2$, so as to provide a compromise between a sufficient moisture vapor transmission rate and a sufficient adhesion to the film or to the skin.

By way of example, use may be made of a substrate consisting of the combination of a polyurethane film 30 μm thick which has a moisture vapor transmission rate of about 7000 g/m$^2$/24 hours, and of a 40 g/m$^2$ polyester knit that is coated with a silicone gel on both its faces and on its entire surface in a proportion of 200 g/m$^2$. This substrate has a thickness of about 400 μm and an MVTR of about 5000 g/m$^2$/24 hours.

The dressing according to the invention comprises a web which is inserted between the absorbent nonwoven and the substrate, and which is intended to assemble them. This securing means is necessary since the surface of the substrate that is coated with an adhesive silicone gel does not adhere sufficiently to the absorbent nonwoven, in particular in a moist environment.

The web inserted between the absorbent nonwoven and the substrate is a non-absorbent nonwoven of low grammage. The nonwoven may be any type of nonwoven commonly used in the field of hygiene and dressings, in particular a spun laid, carded or spun lace nonwoven. Its grammage is preferably between 15 and 50 g/m$^2$, preferably between 20 and 40 g/m$^2$.

The web is non-absorbent in the sense that it does not contain absorbent fibers such as rayon, viscose or cellulose derivatives, and that it does not contain absorbent particles.

It may consist of polyamide, polyester, polyurethane and/or polyolefin fibers. According to one embodiment, the web comprises polyethylene fibers. The fibers may be single-component fibers, or two-component fibers of core/shell or side-by-side type. A spun laid nonwoven, preferably of spun bond type, will for example be chosen.

The non-absorbent web will preferably consist of hydrophobic fibers, but it may also consist of hydrophilic fibers and have undergone a treatment to make it hydrophobic. The web may consist of several layers, insofar as its porosity is sufficient, the layer which comes into contact with the adhesive silicone gel being non-absorbent and preferably hydrophobic.

The web is secured to the absorbent nonwoven over its entire surface, or preferably only along its periphery, by means of conventional securing techniques such as heat, ultrasound, high frequency, or with adhesives. The web is preferably heat-sealable so as to be secured to the complementary nonwoven via heat.

In the context of the present invention, use will be made, for example, of a spun bond web consisting of polyethylene fibers having a grammage of between 30 and 40 g/m$^2$, such as the product sold by the company Freudenberg under the name Vilmed® LSO 1040 Weiss.

An absorbent nonwoven may be chosen from nonwovens of absorbent fibers comprising particles of superabsorbent polymer, and nonwovens comprising superabsorbent fibers.

The absorbent nonwoven may comprise absorbent fibers such as cellulose, rayon or viscose fibers. The nonwoven is preferably obtained via the dry manufacturing method known as "airlaid".

All the bonding modes commonly used in nonwoven technology may be employed for manufacturing the absorbent nonwoven: bonding by spray coating of latex, bonding by incorporation of thermal bonding fibers or powders and then heat treatment, bonding by combining these two techniques, bonding by simple compression of the fibers. The latter bonding mode, which does not call for the incorporation of thermal bonding materials or of latex, will be preferred.

According to one embodiment of the present invention, the absorbent nonwoven incorporates particles of superabsorbent polymers in a proportion of between 1% and 70% by weight, preferably from 25% 55% by weight, of the total weight of the nonwoven. The superabsorbent polymer may be chosen from acrylic polymers, including salts thereof, such as sodium polyacrylates.

According to one preferred embodiment of the present invention, use will be made of a nonwoven based on particles of superabsorbent polymers and cellulose fibers without the incorporation of thermal bonding materials or of latex, which will be covered on each of its faces with a cellulose-based web. According to another variant of the present invention, a nonwoven consisting of two cellulose-based webs, between which are incorporated particles of superabsorbent polymers alone or in combination with binding agents, may also be employed as absorbent nonwoven.

The absorbent nonwoven may also comprise superabsorbent fibers.

In the context of the present invention, use is preferably made of a nonwoven which has a thickness of between 0.5 a 3 mm and/or a grammage of between 200 and 800 g/m$^2$ and/or an absorption of greater than 5000 g/m$^2$, more preferably greater than or equal to 15000 g/m$^2$. The absorption may be measured according to standard EDANA 440.1.99.

Suitable absorbent nonwovens are, for example, sold by the company EAM Corporation under the reference Novathin®.

According to another variant of the present invention, the absorbent nonwoven can be replaced with another absorbent material, such as a woven or a knit.

The absorbent nonwoven preferably has dimensions that are smaller than those of the complementary nonwoven and of the non-absorbent web so as to be able to increase in volume when it absorbs the exudates without compressing the walls of the casing, and risking opening it under the effect of pressure.

The surface of the substrate is advantageously greater than that of the encased absorbent nonwoven, so that the nonwoven does not cover the whole of the surface of the adhesive substrate. Depending on the position of the absorbent nonwoven on the substrate, the shape and the surface of the adhesive borders created may be adapted according to the anatomy of the part of the body to which the dressing is intended to be applied. The encased absorbent nonwoven may be centered on the substrate, so as to create borders of uniform width.

The non-absorbent web and the complementary nonwoven are attached along their side edges while encasing the absorbent nonwoven, preferably without being secured at any point to the latter.

The complementary nonwoven may be any type of nonwoven commonly used in the field of hygiene and dressings, in particular a spun laid or carded nonwoven. Its structure may be reinforced by tufting or by the addition of a thermal bonding polymer in the form of powder or fibers. Its grammage is preferably between 15 and 200 g/m$^2$.

The complementary nonwoven may be absorbent or non-absorbent. The term "non-absorbent" is intended to mean that it does not contain absorbent fibers and that it does not contain absorbent particles.

It may consist of thermoplastic fibers chosen from polyolefins, polyamides, polyesters and polyurethanes and/or of polyolefins. It may comprise absorbent fibers such as rayon, viscose and cellulose derivatives. It may also comprise superabsorbent fibers.

The fibers may be single-component fibers, or two-component fibers of core/shell or side-by-side type.

It may consist of hydrophilic or hydrophobic fibers, preferably hydrophilic fibers. It may also comprise hydrophobic fibers and have undergone a hydrophilic treatment.

The complementary nonwoven is advantageously chosen from hydrophilic nonwovens, preferably of non-absorbent fibers, which have a grammage of between 15 and 50 g/m$^2$, preferably between 20 and 40 g/m$^2$.

According to one embodiment, the complementary nonwoven is preferably a non-absorbent, hydrophilic, thermally bonded nonwoven based on two-component polyethylene/polyester fibers. The references Sawabond® 4413 or 4483 sold by the company Sandler are an example thereof.

According to another embodiment, the complementary nonwoven is chosen from nonwovens comprising superabsorbent fibers and thermal bonding fibers.

An interface layer 1 intended to come into contact with the wound may advantageously be placed on the surface of the complementary nonwoven. The interface layer is discontinuous so as to allow access of the exudates to the complementary nonwoven; it does not detrimentally modify the wound when the dressing is removed. The composition of the interface layer may be hydrophobic, hydrophilic or amphiphilic.

According to one embodiment of the invention, the interface layer is microadhesive to the wound, i.e. it makes it possible to temporarily secure the dressing on the wound, and it can be removed without the structure of the wound or of the perilesional skin being detrimentally modified.

Mention may thus be made of compositions based on silicone polymers, in particular silicone gels, polyurethane gels, elastomer-based compositions including hydrocolloids, or even hydrogels, for example poly(AMPS)-based hydrogels.

In the context of the present invention, preferably use will most particularly be made of a discontinuous layer of composition containing an elastomer, a plasticizer and hydrocolloids. This interface layer promotes the healing process by maintaining a moist environment at the level of the wound, and also makes it possible to convey active agents, which is not the case with silicone-coated interfaces.

The elastomer may be chosen from poly(styrene-olefin-styrene) triblock block polymers optionally combined with diblock copolymers. The triblock copolymers may be poly(styrene-ethylene-butylene-styrene) (abbreviated to SEBS) block copolymers sold under the name Kraton® G1651, Kraton® G1654 or Kraton® G1652, or poly(styrene-ethylene-propylene-styrene) (abbreviated to SEPS) block copolymers.

Among the plasticizer compounds capable of being used, mention may particularly be made of mineral oils, polybutenes or else phthalate derivatives. Particularly preferably, use will be made of a mineral plasticizing oil chosen from the products sold under the names Ondina®933 and Ondina®919.

As suitable hydrocolloids, mention may, for example, be made of pectin, alginates, natural vegetable gums, such as in particular karaya gum, cellulose derivatives, such as carboxymethylcelluloses and alkali metal salts thereof, such as the sodium or calcium salts, known under the reference CMC Blanose® 7H4XF, and also superabsorbent acrylic acid salt-based synthetic polymers, for instance the products sold by the company BASF under the name Luquasorb® 1003 by the company CIBA Specialty Chemicals under the name Salcare® SC91, and also mixtures of these compounds.

The elastomer-based composition including hydrocolloids can include, if necessary, one or more antioxidants, and also the surfactant Montanox® 80 or the polymer Sepinov® EMT 10, both sold by the company SEPPIC, in order to optimize the gelling speed, the wettability or the release of active agents optionally present in the composition.

If it is desired for the interface layer to be microadhesive or adhesive, the elastomer-based composition including hydrocolloids contains a tackifying product which can be chosen from tackifying resins and low-molecular-weight polyisobutylenes, or mixtures thereof. Generally, use will preferably be made of hydrogenated resins such as the Escorez® resins of the 5000 series and most particularly the Escorez® 5380 resin.

The composition may contain active ingredients which have a favourable role in the treatment of the wound. Among the substances which can be used in the context of the present invention, mention may be made, by way of examples, of:

antibacterial agents, for instance silver derivatives, such as the salts of silver or of other metals (for example, silver sulfate, chloride or nitrate and silver sulfadiazine), complexes of silver or of other metals (for example, silver zeolites such as alphasan, or ceramics), metrodinazole, neomycin, polymyxin B, penicillins (amoxycillin), clavulanic acid, tetracyclines, minocycline, chlorotetracycline, aminoglycosides, amikacin, gentamicin or probiotics;

antiseptics, such as chlorhexidine, triclosan, biguanide, hexamidine, thymol, lugol, iodinated povidone, benzalkonium chloride and benzethonium;

painkillers, such as paracetamol, codeine, dextropropoxyphene, tramadol, morphine and its derivatives, corticosteroids and derivatives;

anti-inflammatories, such as glucocorticoids, non-steroidal anti-inflammatories, aspirin, ibuprofen, ketoprofen, flurbiprofen, diclofenac, aceclofenac, ketorolac, meloxicam, piroxicam, tenoxicam, naproxene, indomethacin, naproxcinod, nimesulide, celecoxib, etoricoxib, parecoxib, rofecoxib, valdecoxib, phenylbutazone, niflumic acid, mefenamic acid;

active agents which promote healing, such as retinol, vitamin A, vitamin E, N-acetylhydroxyproline, *Centella asiatica* extracts, papain, essential oils of thyme, of niaouli, of rosemary and of sage, hyaluronic acid, polysulfated oligosaccharides and their salts (in particular synthetic sulfated oligosaccharides having 1 to 4 monosaccharide units, such as the potassium salt of octasulfated sucrose or the silver salt of octasulfated sucrose), sucralfate, allantoin, urea, metformin, enzymes (for example, proteolytic enzymes such as streptokinase, trypsin or collagenase), peptides or protease inhibitors;

anesthetics, such as benzocaine, lidocaine, dibucaine, pramoxine hydrochloride, bupivacaine, mepivacaine, prilocaine or etidocaine.

Use will preferably be made of elastomer-based microadhesive compositions including hydrocolloids which, for a total of 100% by weight, comprise:

0.05% to 1% by weight of antioxidant;

10% to 60% by weight of tackifying resin;

2% to 20%, preferably from 12% to 16%, by weight of sodium carboxymethylcellulose;

10% to 65% by weight of a plasticizing mineral oil;

5% to 25% by weight of a poly(styrene-ethylene-butylene-styrene) or poly(styrene-ethylene-propylene-styrene) triblock polymer; and 1% to 15% by weight of a copolymer consisting of a salt of 2-methyl-2-[(1-oxo-2-propényl)amino]-1-propanesulfonic acid and of the 2-hydroxyethyl ester of propenoic acid.

Another hydrocolloid elastomer composition may comprise, for a total of 100% by weight:

0.05% to 1% by weight of antioxidant;

2% to 20%, preferably from 12% to 16%, by weight of sodium carboxymethylcellulose;

20% to 65% by weight of a plasticizing mineral oil; and

3% to 25% by weight of a poly(styrene-ethylene-butylene-styrene) or poly(styrene-ethylene-propylene-styrene) triblock polymer.

The complementary nonwoven optionally covered with an interface layer may be protected, at least on its face intended to come into contact with the wound, with a protective film-coating which may be removed by peeling off before use of the dressing.

The peel-off protector 3 may consist of one or more parts which can be peeled off before use. This protector covers the entire surface of the dressing.

This protector may be any material commonly used as a protector by those skilled in the art in the dressings field. It may be, for example, in the form of a film, for example a film made of a polyolefin, such as polyethylene or polypropylene, or a polyester film, but also a paper. This film is advantageously treated, on at least one of its faces, with a silicone compound such as a silane, a fluoro compound, or a fluorosilicone compound.

This protector will have to be suitable for the nature of the adhesive silicone gel. This protector will also, where appropriate, have to be suitable for the microadhesive nature of the interface layer.

In the context of the present invention, the use of a two-part protector, as indicated in the FIGURE, will in particular be preferred.

The peel-off protector preferably has a thickness of between 10 and 100 µm, example of about 50 µm.

The product sold under the reference Silflu® M1R88001 by the company Siliconature may advantageously be used as such.

The total thickness of the dressing is advantageously between 3 and 5 mm, preferably about from 4 to 4.5 mm.

The dressing of the invention is advantageously indicated for the treatment of all exudative chronic wounds (eschar, ulcer, for instance a diabetic's foot ulcer) and acute wounds (2nd-degree burn, dermabrasion, trauma wound, post-operative wound).

The dressing of the invention is particularly indicated for the treatment of wounds when the perilesional skin is weakened.

In the context of the present invention, the use of a dressing with rounded corners will be preferred in order to avoid premature detachment.

The dressing of the invention may be in the form of individual dressings of small size or of larger size. The dressings will be packaged individually in a sealed wrapping ensuring preservation in a sterile environment.

A subject of the present invention is also a process for manufacturing the dressing previously described, which consists in producing the substrate, in securing the non-absorbent web and the complementary nonwoven to one another while encasing the absorbent nonwoven, preferably without them being secured at any point to the latter, and then in assembling the encased absorbent nonwoven to the substrate, on the side of the non-absorbent web.

According to one embodiment, the encased absorbent nonwoven is assembled to the support by bringing the non-absorbent web into contact with the side of the substrate that is covered with adhesive silicone gel.

In a first step, the substrate is produced by coating the reinforcement and assembling the coated reinforcement to the continuous film.

The silicone gel will be coated onto the reinforcement using one of the coating techniques commonly employed by those skilled in the art.

According to the preferred version of the present invention, the silicone gel is coated onto the two faces of the reinforcement, which is assembled to the continuous film even though the crosslinking of the gel is not complete, so as to ensure cohesion between the film and the openwork reinforcement. In this embodiment, no adhesive is necessary to make the reinforcement adhere to the film that is impermeable to liquids, but permeable to water vapor.

In this version, the substrate can be manufactured according to the succession of steps that follow:

the reinforcement is covered on both its faces with a mixture of the silicone gel precursors, the reinforcement is assembled to the film, for example by calendering, and the crosslinking of the silicone gel is brought about or accelerated once the reinforcement and the film have been assembled, by placing, for example, the substrate in an oven.

The reinforcement is, for example, immersed in the mixture of the silicone gel precursors, and then wrung in a lamination station between two rollers. A blower makes it possible to reconstitute the openings of the reinforcement in order to remove the surplus silicone gel.

In another version, the silicone gel is coated onto one of the two faces of the reinforcement, and the other face is secured to the continuous film via an adhesive. It can also be secured by heat, ultrasound or high frequency, and, in this case, the reinforcement and/or the continuous film may be thermoplastic, so as to heat-seal them.

The substrate will be protected by covering its adhesive face with a protective layer or film-coating. This protective layer may be, for example, paper or a polyester film.

In a second step, the absorbent nonwoven is encased.

A reel of web and a reel of absorbent nonwoven are unwound and then relaxed, before being superposed. The absorbent nonwoven is then cut along its thickness, preferably in the shape of squares, which are then placed on the web. A reel of complementary nonwoven is unwound and relaxed and then the layer of complementary nonwoven is superposed on the assembly consisting of the layer of web and the layer of absorbent nonwoven previously cut. The non-absorbent web and the complementary nonwoven are secured together only along their periphery via heat, ultrasound, high frequency or with an adhesive. The heat-sealing of the web and of the complementary nonwoven is, for example, carried out along a line far away from the edges of the absorbent nonwoven so as to create a casing of sufficient size which allows the absorbent nonwoven to swell during the absorption of liquids.

The web and the complementary nonwoven are preferably sealed by heat or ultrasound. The sealing temperature will, for example, be between 80 and 150° C., more preferably between 90 and 120° C., in particular about 110° C. The web and the complementary nonwoven are secured, for example, over a width of from 1 to 3 mm.

The encased absorbent nonwoven is subsequently stripped and then assembled to the previously manufactured substrate, on the side of its adhesive surface, in a lamination station, by applying a set pressure ranging from 0 to 10 bar, preferably from 0 to 6 bar. The lamination station is advantageously a drawing station.

Before carrying out the cutting, the substrate/encased nonwoven assembly is covered, on the side of the complementary nonwoven intended to come into contact with the wound, with a protective film-coating which may be removed by peeling off before use of the dressing.

If the complementary nonwoven was previously covered with an interface layer and with a temporary peel-off protector, said temporary protector will be removed in order to cover the substrate/encased nonwoven/interface layer assembly, on the side of the interface layer intended to come into contact with the wound, with a protective film-coating which may be removed by peeling off before use of the dressing.

When it is desired to secure the non-absorbent web to the complementary nonwoven with an adhesive, the unwound and relaxed complementary web is coated with adhesive before being calendered with the assembly consisting of the layer of web and the layer of absorbent nonwoven previously cut.

The surface of the complementary nonwoven intended to come into contact with the wound, optionally covered with an interface layer, may be protected by covering it with a protective film-coating which may be removed by peeling off before use of the dressing.

Once the non-absorbent web and the complementary nonwoven have been secured to one another, while encasing the absorbent nonwoven, preferably without being secured at any point to the latter, the assembly is preferably assembled to the substrate by means of the same lamination process as previously described. The choice of a non-absorbent web in accordance with the present invention advantageously makes it possible to assemble the substrate and the web without it being necessary to have recourse to an acrylic adhesive as in the prior art. The substrate and the non-absorbent web remain connected together when the used dressing is removed, or detached from the skin.

According to one embodiment, the non-absorbent web advantageously undergoes a Corona treatment, preferably just after it has been unwound. The Corona treatment makes it possible to increase the attachment of the web to the substrate that is coated with adhesive silicone gel. In this embodiment, the web may consist of polyethylene fibers.

The encased absorbent nonwoven may be covered with an interface layer on the surface of the complementary nonwoven intended to come into contact with the wound, before being complexed with the different element constituting the compress.

An elastomer-based interface layer containing hydrocolloids, described above, can be manufactured according to a hot melt process well known to those skilled in the art, by hot-blending of the various constituents at a temperature between 90 and 160° C. and preferably between 110 and 140° C. An etched cylinder is preferably dipped in the previously hot-blended composition, and then the still-hot composition is demolded and transferred onto the complementary nonwoven. The application of the still-hot composition onto the complementary nonwoven makes it possible to optimise the attachment of the interface layer. A temporary protector can be placed on the complementary nonwoven that is coated with the interface layer, in order to carry out the calendering step with the adhesive substrate.

The temporary protector is removed after the securing of the complementary nonwoven that is coated with the interface layer to the substrate, in order to apply a peel-off protector which will be removed before the application of the dressing to the wound.

The invention is illustrated by the following example.

Example 1

Preparation of an Absorbent Dressing

A side-strip dressing comprising an absorbent nonwoven encased in a non-absorbent polyethylene web and a hydrophilic complementary nonwoven is manufactured. A microadhesive interface layer is deposited on the surface of the complementary nonwoven intended to come into contact with the wound.

The following materials are used:
The substrate is a 40 g/m$^2$ polyester knit that is coated on both its faces and on its entire surface with an adhesive silicone gel (200 g/m$^2$), which was laminated on a polyurethane film 30 μm thick. This substrate layer has a thickness of about 300 μm and an MVTR of about 5000 g/m$^2$/24 hours.

The polyethylene web is a 40 g/m² nonwoven sold under the reference Vilmed® LSO 1040 Weiss by Freudenberg.

The absorbent nonwoven is an airlaid (400 g/m²) containing 50% of superabsorbent polymer from EAM Corporation sold under the reference Novathin®.

The complementary nonwoven is a hydrophilic nonwoven having the reference Sawabond® 4483, sold by the company Sandler.

The peel-off protector comprises 50 nm wings made of fluorinated PET, provided by Siliconature under the reference Silflu® M1R88001.

Preparation of the Interface Layer and Coating onto the Complementary Nonwoven:

The following composition, expressed as percentage by weight relative to the total weight, is prepared:

Mineral oil sold by the company Shell under the name Ondina®919: 39.7%.

Sodium salt of carboxymethylcellulose sold by the company Aqualon under the name CMC Blanose® 7H4XF: 14.8%.

Poly(styrene-ethylene-butylene) block copolymer sold by the company Kraton under the name Kraton® G 1651E: 4.7%.

Antioxidant sold under the name Irganox® 1010 by the company Ciba Specialty Chemicals: 0.2%.

Copolymer of 2-methyl-2[(1-oxo-2-propenyl)amino]-1-propanesulfonic acid salt and of the 2-hydroxyethyl ester of propenoic acid (releasing agent) sold by the company SEPPIC under the name Sepinov® EMT 10: 5%.

Tackifying resin sold by the company Exxon Chemicals under the name Escorez® 5380: 35.6%.

The mineral oil, the hydrocolloid and the elastomer and then the antioxidant and the releasing agent and, finally, the tackifying resin, which were brought to a temperature of between 100 and 110° C., were introduced into an MEL G-40 blender, so as to obtain a homogeneous mixture.

The previous mixture is discontinuously coated, in an amount of 170 g/m² (±40), onto the complementary nonwoven.

Assembling of the Layers:

Squares of complementary nonwoven and of polyethylene web are cut out and sealed over a width of 2 mm with an Amis manual sealer on just one side. The polyethylene web previously underwent a Corona treatment under the following conditions:

Generator power: 570 watts
Number of electrodes/width: 3/0.25 m
Gap adjustment: 2 mm
Travel speed: 2 m/minute The absorbent nonwoven is then inserted between the complementary nonwoven and the web.

The other three sides of the complementary nonwoven and of the polyethylene web are sealed under the same conditions as previously, so as to form an 8×8 cm square, and then the edges of the assembled complex are cut off.

The substrate is cut into a 15×15 cm square and then assembled to the previous complex by calendering with a 10 kg roller, in two perpendicular directions.

Cutting of the final dressing is then carried out.

The invention claimed is:

1. An adhesive absorbent dressing comprising an absorbent nonwoven and a protective substrate that is impermeable to fluids, but permeable to water vapor, characterized in that:
   the substrate is formed by assembling a continuous film and an openwork reinforcement that is coated, on at least one of its faces, with adhesive silicone gel without blocking the openings in the reinforcement, said reinforcement covering the entire surface of the film,
   in that said dressing also comprises a non-absorbent web and a complementary nonwoven which are secured to one another along their periphery while encasing said absorbent nonwoven without being secured at any point to the latter, and
   in that said non-absorbent web adheres to the adhesive silicone gel that is coated onto said reinforcement.

2. The dressing as claimed in claim 1, wherein the non-absorbent web has a grammage of between 15 and 50 g/m².

3. The dressing as claimed in claim 1, wherein the grammage of the adhesive silicone gel is between 100 and 500 g/m².

4. The dressing as claimed in claim 1, wherein the complementary nonwoven is chosen from hydrophilic nonwovens based on non-absorbent fibers, the grammage of which is between 15 and 50 g/m².

5. The dressing as claimed in claim 1, wherein the complementary nonwoven is chosen from nonwovens comprising superabsorbent fibers and thermal bonding fibers.

6. The dressing as claimed in claim 1, wherein the openwork reinforcement is a knit that is coated with adhesive silicone gel on both its faces and on its entire surface without blocking the openings of the knit.

7. The dressing as claimed in claim 1, wherein the openwork reinforcement is a perforated film that is coated with adhesive silicone gel on just one of its faces, without blocking the perforations of the film.

8. The dressing as claimed in claim 1, for use on a wound, such as exudative chronic wounds, in particular an eschar, an ulcer, for instance a diabetic's foot ulcer, and acute wounds, such as a second-degree burn, a dermabrasion, a trauma wound or a post-operative wound.

9. A process for manufacturing a dressing as claimed in claim 1, which consists in producing the substrate, in securing the non-absorbent web and the complementary nonwoven to one another while encasing the absorbent nonwoven, and then in assembling the encased absorbent nonwoven to the substrate, on the side of the non-absorbent web.

10. The process as claimed in claim 9, wherein the non-absorbent web and the complementary nonwoven are secured together only along their periphery via heat, ultrasound, high frequency or with an adhesive.

11. The process as claimed in claim 9, wherein the substrate is assembled to the encased absorbent nonwoven in a lamination station by applying a pressure ranging from 0 to 10 bar.

12. The process as claimed in claim 9, wherein the non-absorbent web undergoes a Corona treatment, just after it has been unwound.

* * * * *